(12) United States Patent
Gitomer et al.

(10) Patent No.: US 7,195,770 B2
(45) Date of Patent: Mar. 27, 2007

(54) BODY SCRUB COSMETIC COMPOSITION

(75) Inventors: Teresa Jahn Gitomer, Charlotte, NC (US); Pamela Elaine Dalton, Dallas, OR (US)

(73) Assignee: Basalt Works, LLC, Dallas, OR (US)

( * ) Notice: Subject to any disclaimer, the term of this patent is extended or adjusted under 35 U.S.C. 154(b) by 538 days.

(21) Appl. No.: 10/238,321

(22) Filed: Sep. 10, 2002

(65) Prior Publication Data

US 2004/0028630 A1    Feb. 12, 2004

Related U.S. Application Data

(60) Provisional application No. 60/401,384, filed on Aug. 6, 2002.

(51) Int. Cl.
*A61Q 19/10* (2006.01)

(52) U.S. Cl. ...................... 424/401; 510/130

(58) Field of Classification Search ................ 424/401, 424/78.03
See application file for complete search history.

(56) References Cited

U.S. PATENT DOCUMENTS

| 3,645,904 | A | | 2/1972 | Beach ......................... 252/89 |
|---|---|---|---|---|
| 4,188,447 | A | | 2/1980 | Ehlenz ........................ 428/310 |
| 4,342,743 | A | * | 8/1982 | Panton-Moore .............. 424/61 |
| 4,508,634 | A | | 4/1985 | Elepano et al. ............. 252/163 |
| 4,537,604 | A | | 8/1985 | Dawson ........................ 51/298 |
| 4,786,369 | A | | 11/1988 | Kanfer et al. ............... 252/120 |
| 4,996,000 | A | * | 2/1991 | Redeker ..................... 510/139 |
| 5,683,683 | A | * | 11/1997 | Scafidi .................... 424/70.19 |
| 5,858,939 | A | * | 1/1999 | Tsaur ......................... 510/141 |
| 6,063,366 | A | | 5/2000 | Sugai et al. .................. 424/69 |
| 6,087,310 | A | | 7/2000 | Henkel ........................ 510/138 |
| 6,265,363 | B1 | | 7/2001 | Viscovitz .................... 510/130 |
| 6,294,179 | B1 | | 9/2001 | Lee et al. .................... 424/401 |
| 6,294,509 | B1 | | 9/2001 | Meiwa et al. ............... 510/130 |
| 6,309,655 | B1 | | 10/2001 | Minnix ....................... 424/401 |

FOREIGN PATENT DOCUMENTS

WO    WO 98/56850    * 12/1998

OTHER PUBLICATIONS

Volcanic and Geologic Terms, http://volcano.und.nodak.edu/vwdocs/glossary.html.*

* cited by examiner

*Primary Examiner*—Jyothsna Venkat
(74) *Attorney, Agent, or Firm*—Kennedy Covington Lobdell & Hickman, LLP

(57) ABSTRACT

A cosmetic composition comprising basalt suitable for use as a body scrub to remove dead skin from the human body such as, for example, from the hands, feet, elbows, and knees and its method of its preparation.

8 Claims, No Drawings

BODY SCRUB COSMETIC COMPOSITION

CROSS-REFERENCE TO RELATED APPLICATIONS

The present application claims the benefit of U.S. provisional application No. 60/401,384, filed Aug. 6, 2002.

FIELD OF THE INVENTION

The present invention relates to a cosmetic composition that can be used as a body scrub wherein the cosmetic composition comprises basalt.

BACKGROUND OF THE INVENTION

Various forms of cosmetic compositions for cleaning the skin have been known for years. For example, U.S. Pat. No. 3,645,904 discloses a skin cleaner having plastic synthetic resin material in a fine state of comminution included therein so as to impart a scrubbing or mechanical detersive action thereto.

U.S. Pat. No. 4,508,634 discloses an aqueous skin cleaner composition comprising propylene carbonate suitable for removing paint, grease, dirt and other foreign materials from the skin.

U.S. Pat. No. 6,063,366 discloses a cosmetic composition comprising disintegrating granules composed of water-insoluble primary particles such as polyethylene, polystyrene, polyester, polyvinyl chloride, polyamide, polypropylene, and nylon, wherein the disintegrating granules in the cosmetic composition have a compression strength of 0.002–0.1 $kgf/mm^2$ and a particle size of 100–2,000 μm.

U.S. Pat. No. 6,087,310 discloses skin cleaning composition comprising a polymer latex emulsion suitable for removing dirt, grease and oils from the hands or other skin surfaces without the need for additional water or other solvent.

U.S. Pat. No. 6,265,363 discloses a skin cleansing composition suitable for removing ink and other stains from the hands and arms of a user and includes an effective amount of a low molecular weight alcohol having from one to twelve carbon atoms and an effective amount of a peroxide releasing agent, such that together, the alcohol and the peroxide releasing agent provide a synergistic reaction that effectively removes the ink from the skin of the user.

U.S. Pat. No. 6,309,655 discloses a cosmetic composition comprising self-heating, self-indicating disintegrating granules comprised of water-insoluble polymer and a colorant, which gives users indications of the length of time the composition has been applied and the degree of mixing when in use.

However, until now, there has not been a cosmetic composition for use as a body scrub comprising basalt and that has the natural abrasive effectiveness and aesthetic desirability of the cosmetic composition of the present invention.

SUMMARY OF THE INVENTION

Further areas of applicability of the present invention will become apparent from the detailed description provided hereinafter. It should be understood that the detailed description, while indicating the preferred embodiment of the invention, are intended for purposes of illustration only and are not intended to limit the scope of the invention.

Accordingly, it is an object of the present invention to provide a cosmetic composition comprising basalt for use as a body scrub. It is another object of the present invention to provide a cosmetic composition comprising basalt, salt and an oil for use as a body scrub. It is yet another object of the present invention to provide a method of preparing a cosmetic composition comprising basalt.

DESCRIPTION OF THE PREFERRED EMBODIMENTS

The following description of the preferred embodiments is merely exemplary in nature and is in no way intended to limit the invention, its application, or uses.

The cosmetic composition of the present invention is particularly suitable for use as a "body scrub." The term "body scrub" as used herein refers to an abrasive cleaning composition used to remove dead skin from the human body such as, for example, from the hands, feet, elbows, and knees.

The cosmetic composition of the present invention comprises basalt. Basalt is found in the earth's crust and is a dark, fine-grained igneous rock originating from a lava flow or other volcanic activity. It is often composed of plagioclase clinopyroxene and sometimes olivine, and often displays a columnar structure. Basalt can be found, for example, in quarries in the United States. Basalt suitable for use in the cosmetic composition of the present invention is commercially available and may be obtained, for example, from Dalton Rock, Inc. of Dallas, Oregon.

It is also possible to obtain basalt suitable for use in the present invention by the following means. A basalt lava flow may be blasted into pieces such that it can be processed through an industrial rock crushing plant. Such a plant typically is comprised of three units wherein each unit comprises screening apparatus appropriate for sizing particles of the basalt at that stage in the reduction process. The primary crusher is of the eccentric jaw type, with a typical closed-side setting of six inches. From there, the basalt is conveyed to a secondary crusher of a cone type, incorporating both reciprocating and oscillating motions. Upon discharge from the secondary cone, the basalt enters another cone unit for the third stage of size reduction. The discharge from the third unit typically passes through a screen with one inch square openings. The resulting particles range in size from the one inch sieve size down to dust.

Particles that may be larger than desired for use in the cosmetic composition of the present invention are further crushed by any crushing means known to one of ordinary skill in the art. Such means include, but are not limited to, an industrial roll-type crusher, rod mill, ball mill, and/or a rotating-plate grinder-pulverizer. The basalt is typically crushed to a size of about 0.010 inches (0.0254 cm) or smaller.

Once the crushing process is complete, the resulting material is sifted using, for example, conventional vibrating and/or oscillating sieving screens. Particles are graded by passing one size sieve screen over another, smaller screen, and those particles retained on the smaller screen may be suitable for use in the cosmetic composition of the present invention. Sizes are often referred to as "passing _____, retained on _____" by one of ordinary skill in the art. For example, "passing #80, retained on #120" contains particles between 0.007 inches (0.0178 cm) and 0.0049 inches (0.0124 cm). All sieve ranges and particle size designations are made with reference to U.S. Sieve Series, ASTM Specification E-11-95, which is herein incorporated by reference.

After dry screening, the particles are washed in water without any soaps or detergents over a sieve such as a #200 that removes any dust particles adhering to the desired gradated crystals of basalt. After washing, the crystals of basalt are baked in a conventional oven at 400 degrees Fahrenheit (204.4° C.) for a minimum of one hour.

The cosmetic composition of the present invention may also comprise a carrier. The carrier may be, for example, water or oil. Preferably, the carrier is an oil. Preferably, the cosmetic composition of the present invention comprises at least one oil. Preferred oils for use in the present invention include, but are not limited to, prunus amygdalus dulcis (sweet almond) oil, carthamus tinctorius (safflower) seed oil, glycine soja (soybean) oil, mentha piperita (peppermint) oil, mentha viridis (spearmint) leaf oil, citrus grandis (grapefruit) peel oil, rosmarinus officinalis (rosemary) leaf oil, citrus aurantium dulcis (orange) oil, and citrus medica limonum (lemon) peel oil.

Other materials may be present in the cosmetic composition of the present invention. In the selection of ingredients in the cosmetic composition, it is contemplated that materials will be utilized that are compatible, both chemically and physically, with the basalt. Such materials include, but are not limited to, vitamins, fragrances, colorants, preservatives, oils and salts. Preferred materials include, but are not limited to, sodium chloride, laureth-4, sodium sesquicarbonate, sea salt such as dead sea salts, magnesium sulfate, tocopherol, and butylated hydroxytoluene (BHT).

The basalt is present in the cosmetic composition of the present invention in an amount greater than 0% to about 15%, based upon the total weight of the composition. Preferably, the weight percentage of the basalt is from about 1% to about 10%, based upon the total weight of the composition. The weight percentages of the carrier and any other materials present in the cosmetic composition may be varied by one of ordinary skill in the art and still be within the scope of the present invention as it may be desired to adjust these weight percentages to achieve different aesthetic aspects of the cosmetic composition such as fragrance and texture.

Preferably, the cosmetic composition has a specific gravity of 1.121–1.14. Preferably, the cosmetic composition has a boiling point greater than 212 degrees Fahrenheit (100° C.).

The cosmetic composition may be prepared by mixing the materials by any conventional means or any means known to one of ordinary skill in the art including, but not limited to, mechanical mixers. Preferably, the solid materials are mixed together prior to the addition of the liquid materials. Preferably, once the liquid materials are added, the entire mixture is again mixed.

An advantage of the cosmetic composition of the present invention is that it comprises basalt which is a natural ingredient as opposed to a synthetic abrasive. This is particularly desirable since the cosmetic composition is for use on the human body. The cosmetic composition of the present invention is ideally suited for use at home as well as at a salon or a spa. The cosmetic composition of the present invention is ideal for use in conjunction with a manicure or pedicure or as a precursor to a self-tanning or body moisturizing treatment. Another advantage of the cosmetic composition of the present invention is it may be rinsed from the body with water and leaves the skin smooth but without a greasy feeling.

PROPHETIC EXAMPLE

A body scrub composition in accordance with the present invention is prepared by mixing in a conventional mixer the following components: sodium chloride, crushed basalt, sea salt, laureth-4, magnesium sulfate, and BHT. The crushed basalt is commercially available from Dalton Rock, Inc.

Once the above components are mixed well, the following are then added to the mixture: prunus amygdalus dulcis (sweet almond) oil, carthamus tinctorius (safflower) seed oil, glycine soja (soybean) oil, mentha piperita (peppermint) oil, mentha viridis (spearmint) leaf oil, citrus grandis (grapefruit) peel oil, rosmarinus officinalis (rosemary) leaf oil, citrus aurantium dulcis (orange) oil, and citrus medica limonum (lemon) peel oil. Tocopherol is also added. The mixture is then mixed together in a mixer to form the cosmetic composition.

The cosmetic composition has the following composition, and all weight percentages are based upon the total weight of the composition. Sodium chloride is present in an amount of 55% by weight. Basalt is present in an amount of 9% by weight. Sea salt is present in an amount of 5% by weight. Laureth-4 is present in an amount of 3% by weight. Magnesium sulfate is present in an amount of 1% by weight. The BHT is present in an amount of 0.2% by weight. The prunus amygdalus dulcis (sweet almond) oil is present in an amount of 18% by weight. The carthamus tinctorius (safflower) seed oil, glycine soja (soybean) oil, mentha piperita (peppermint) oil, mentha viridis (spearmint) leaf oil, citrus grandis (grapefruit) peel oil, rosmarinus officinalis (rosemary) leaf oil, citrus aurantium dulcis (orange) oil, and citrus medica limonum (lemon) peel oil are each present in an amount of 1% by weight. Tocopherol is also present in an amount of 0.8% by weight.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

We claim:

1. A body cleaning composition comprising:
   crushed basalt.
   salt, and
   an oil wherein the oil is selected from the group consisting of mentha piperita (peppermint) leaf oil, mentha viridis (spearmint) leaf oil, citrus grandis (grapefruit) peel oil, rosmarinus officinalis (rosemary) leaf oil, citrus aurantium dulcis (orange) peel oil, citrus medica limonum (lemon) peel oil, glycine soja (soybean) oil, carthamus tinctorius (safflower) seed oil and prunus amygdalus dulcis (sweet almond) oil;
   wherein the crushed basalt has a particle size of about 0.010 inches or less and is present in an amount greater than 0 to about 15% by weight based upon the weight of the body cleaning composition.

2. A body cleaning composition comprising:
   a) basalt,
   b) sodium chloride, c) prunus amygdalus dulcis (sweet almond) oil,
d) laureth-4,
e) carthamus tinctorius (safflower) seed oil,
f) glycine soja (soybean) oil,
g) mentha piperita (peppermint) oil,
h) mentha viridis (spearmint) leaf oil,
i) citrus grandis (grapefruit) peel oil,
j) rosmarinus officinalis (rosemary) leaf oil,
k) citrus aurantium dulcis (orange) oil,
l) citrus medica limonum (lemon) peel oil,
m) sea salt,
n) magnesium sulfate,
o) tocopherol, and
p) butylated hydroxytoluene.

3. The body cleaning composition as claimed in claim 2, wherein the basalt is crushed.

4. The body cleaning composition as claimed in claim 3, wherein the crushed basalt has a particle size of about 0.010 inches or less.

5. The body cleaning composition as claimed in claim 2, wherein the basalt is present in an amount greater than 0% to about 15% by weight based upon the weight of the composition.

6. The body cleaning composition as claimed in claim 2, wherein:
   a) the basalt is present in amount greater than 0 to about 15%,
   b) the sodium chloride is present in amount from about 40% to about 60%,
   c) the prunus amygdalus dulcis (sweet almond) oil is present in amount from about 0 to about 25%,
   d) the laureth-4 is present in amount from about 0 to about 5%,
   e) the carthamus tinctonus (safflower) seed oil is present in amount from about 0 to about 5%,
   f) the glycine soja (soybean) oil is present in amount from about 0 to about 5%,
   g) the mentha piperita (peppermint) oil is present in amount from about 0 to about 5%,
   h) the mentha viridis (spearmint) leaf oil is present in amount from about 0 to about 5%,
   i) the citrus grandis (grapefruit) peel oil is present in amount from about 0 to about 5%,
   j) the rosmarinus officinalis (rosemary) leaf oil is present in amount from about 0 to about 5%,
   k) the citrus aurantium dulcis (orange) oil is present in amount from about 0 to about 5%,
   l) the citrus medica limonum (lemon) peel oil is present in amount from about 0 to about 5%,
   m) the sea salt is present in amount from about 0 to about 10%,
   n) the magnesium sulfate is present in amount from about 0 to about 5%,
   o) the tocopherol is present in amount from about 0 to about 5%, and
   p) the butylated hydroxytoluene is present in amount from about 0 to about 1%.

7. A method of preparing a body cleaning composition, the method comprising mixing crushed basalt with salt an and oil insert wherein the crushed basalt has a particle size of about 0.010 inches or less and present in an amount greater than 0% to about 15% by weight based upon the weight of the body cleaning composition.

8. The method as claimed in claim 7, wherein the oil is selected from the group consisting of mentha piperita (peppermint) leaf oil, mentha viridis (spearmint) leaf oil, citrus grandis (grapefruit) peel oil, rosmarinus officinalis (rosemary) leaf oil, citrus aurantium dulcis (orange) peel oil, citrus medica limonum (lemon) peel oil, glycine soja (soybean) oil, carthamus tinctorius (safflower) seed oil and prunus amygdalus dulcis (sweet almond) oil.

* * * * *